United States Patent [19]

Bayne

[11] Patent Number: 4,873,992
[45] Date of Patent: Oct. 17, 1989

[54] CERVICAL CYTOLOGY DEVICE

[75] Inventor: Irman D. Bayne, Littleton, Colo.

[73] Assignee: Medical Dynamics, Inc., Englewood, Colo.

[21] Appl. No.: 153,417

[22] Filed: Feb. 8, 1988

Related U.S. Application Data

[62] Division of Ser. No. 28,458, Mar. 20, 1987, Pat. No. 4,754,764.

[51] Int. Cl.$^4$ ............................................. A61B 10/00
[52] U.S. Cl. .................................. 128/756; 128/759; 128/357; 15/206; D4/128; D4/133
[58] Field of Search ............... 128/357, 749, 756, 757, 128/759; D4/119, 120, 127, 128, 130-135; 15/206

[56] References Cited

U.S. PATENT DOCUMENTS

| | | | |
|---|---|---|---|
| 2,070,393 | 6/1934 | Cave | 15/206 |
| 2,174,214 | 9/1939 | Quinn | 15/180 |
| 3,626,470 | 12/1971 | Antonides | . |
| 3,881,464 | 5/1975 | Levene | 128/756 |
| 3,881,464 | 5/1975 | Levene | 128/304 |
| 4,127,113 | 11/1978 | Nollan | 128/756 |
| 4,157,709 | 6/1979 | Schuster et al. | 128/759 |
| 4,384,587 | 5/1983 | Milgrom | 128/757 |
| 4,448,205 | 5/1984 | Stenkvist | 128/304 |

OTHER PUBLICATIONS

Drs. Christine Bergeron, M.D. and Alex Ferenczy, M.D. "Screening devices for Cervical and Endometrial Ca" published in Contemporary OB-GYN (1987); pp. 55-66.

Primary Examiner—Max Hindenburg
Assistant Examiner—Randy Citrui
Attorney, Agent, or Firm—Fields, Lewis, Pittenger & Rost

[57] ABSTRACT

A method and device for simultaneously collecting cytology cell samples from the endocervix and exocervix are disclosed. The device includes a handle for manipulating and rotating the device. Adjacent the handle is an intermediate cell collecting surface which is sized and configured to scrape cell samples from the exocervix when it is in contact with the exocervix and the device is rotated. The device also includes a distal cell collecting surface adjacent the intermediate cell collecting surface. The distal section is sized and configured to scrape cytology cell samples from the endocervical canal when it is located within the canal and in contact with the walls thereof and the device is rotated. The distal and intermediate surface are further positioned on the device with respect to each other to enable the endocervical canal and exocervix to be scraped simultaneously as the device is rotated.

9 Claims, 1 Drawing Sheet

CERVICAL CYTOLOGY DEVICE

This is a division of the application Ser. No. 028,458 filed Mar. 20, 1987 now U.S. Pat. No. 4,754,764.

TECHNICAL FIELD

The invention relates generally to a method apparatus for collecting cell specimens for diagnostic purposes and more particularly to a cervical cytology device and method for collecting cytology cell samples from the uterine endocervix and exocervix.

BACKGROUND ART

It is well-known that uterine cervical cancer can be prevented and/or even cured if it is detected early enough, preferably in its precancerous or precursor stages. Accordingly, women are being encouraged to come in for examinations on a regular basis. Improvements in early detection devices and techniques will also, quite obviously, enhance the physician's ability to accurately detect the presence of cancer in its early stages. Accordingly, much effort is being directed to developing such devices.

Drs. Christine Bergeron, M.D. and Alex Ferenczy, M.D. in their article entitled "*Screening Devices for Cervical and Endometrial Ca*" published in Contemporary OB-GYN (1987), set forth on pages 55–66 an extensive listing of cervical cytologic sampling and screening devices, including wooden spatulas and brushes, and also discuss how the devices should be used to effectively detect the presence of cancer and its precursors.

U.S. Pat. No. 3,881,464 to Levene also discloses a device for obtaining endocervical cell and tissue samples. The device comprises a generally frusto conical brush having a coaxial handle projecting from its larger end. The frusto conical brush consists of soft radially projecting bristles of cellulose acetate which are soluble in a liquid that does not cause morphological damage when the bristles and cell samples are immersed in the liquid. While useful in obtaining cell samples from the endocervical canal, the brush's frusto conical shape does not lend itself to collecting cells from the exocervix.

While the aforementioned devices undoubtedly work as intended, there is still a need for devices which are capable of collecting samples containing more cells, particularly from the exocervix area. The aforementioned wooden spatula does not generally collect enough cells from the exocervix to enable one to accurately determine whether any abnormal cells are present. The problem is even worse with women who have an abnormally or unusually shaped exocervix since the spatula's long rigid lobe may not even make contact with the exocervix. Accordingly, a need still exists for a device which is capable of collecting larger cell samples from the uterine exocervix. Such a device would be even more desirable if it also had the capability of collecting cell samples from the endocervical canal. Such a device would make better use of the physician's time and be more palatable to the patient since it would enable the samples to be taken quicker. Such a device would also be more accurate than presently available devices since it would make it possible to collect larger cell samples from the exocervix.

DISCLOSURE OF THE INVENTION

The present invention addresses the aforementioned concerns and needs by providing a cervical cytology device for simultaneously collecting cytology cell samples from the uterine endocervix and exocervix. In its broad form the device includes a handle for manipulating and rotating the device, an intermediate cell collecting surface region adjacent the handle for scraping cytology cells from the exocervix and a distal cell collecting surface adjacent the intermediate cell collecting surface for scraping cytology cells from the endocervical canal. The cell collecting surfaces are sized and configured to be capable of scraping cytology cell samples from their respective cervical areas when they are in contact with their respective regions of the cervix the device is rotated. The distal and intermediate cell collecting surfaces also positioned with respect to each other on the device so as to enable the endocervical canal and exocervix to be scraped simultaneously as the device is rotated.

A preferred embodiment of the cervical cytology device of the present invention is a brush which includes a rigid yet bendable shaft having less than three bends which define four sections of the brush. The first bend joins an outwardly projecting or distal cell collecting surface and an intermediate cell collecting surface of the brush. The bend is provided such that the cell collecting surfaces define less than a 90° included angle between their respective shafts. The second bend on the brush's shaft adjoins the intermediate cell collecting surface and an offset intermediate section, and the bend is such that the intermediate sections define approximately a 10° included angle. The third bend joins the intermediate offset section and an outwardly projecting handle section of the brush. This third bend is such that the offset and handle sections define at least a 90° included angle. The bends are also provided so that the distal and handle sections of the brush are axially aligned. In addition, the distal cell collecting surface of the brush is sized and configured to collect cytology cell samples from the endocervical canal when the brush is rotated and the distal cell collecting surface is located within the canal and in contact with the wall thereof. The intermediate cell collecting surface is also sized and configured to collect cytology cell samples from the surface of the exocervix as the distal cell collecting surface is rotated to collect cytology cell samples from the endocervical canal. Accordingly, cell samples from the endocervical and exocervical surface can be collected simultaneously.

The angles described above between the different sections of the brush can be altered at will by the physicians by bending the shaft of the brush. The physician, in effect, can mold the brush to "customize" a "fit" for each individual patient.

The present invention also provides a method of collecting cytology cell samples from the endocervix and exocervix simultaneously. The method includes providing a rotatable cervical cytology device having a first cell collecting surface which is sized and configured to collect cells from the exocervix and a second cell collecting surface which is sized and configured to collect cells from the endocervical canal where the device is rotated. The method further includes inserting the second cell collecting surface into the endocervical canal until the first cell collecting surface is positioned against the surface of the exocervix. The device is then rotated so that cytology cell samples are scraped from the respective surfaces of the exocervix and endocervix simultaneously. As such, the cell samples will collect on the respective first and second cell collecting surface of the device. The device is then withdrawn from the patient. The samples are then removed from the device and examined to determine whether any abnormal cancerous, precancerous or virally diseased cells are present.

Additional advantages of this invention will become apparent from the detailed description which follows, taken in conjunction with the accompanying drawings.

BEST MODE FOR CARRYING OUT THE INVENTION

Figure 1:
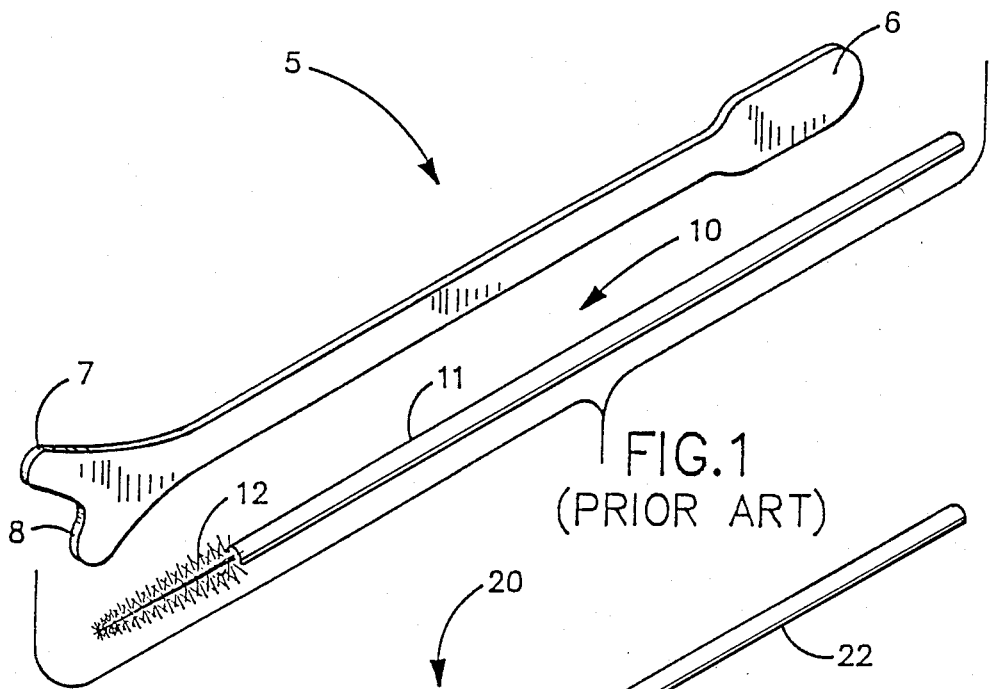
FIG. 1 is a perspective view of a conventional prior art wooden spatula and an endocervical brush which are used by physicians to scrape cytology cell samples from different areas of a uterus.

FIG. 1 illustrates a conventional wooden spatula 5. Drs. Bergeron and Ferenczy describe spatula 5 on page 56 of their above-mentioned article as being a tool for sampling the squamocolumnar junction, the exocervix and to a lesser degree the endocervix. As seen in FIG. 1, one end of spatula 5 is provided with a handle portion 6 for manipulating the spatula. At its other end, spatula 5 is provided with a long lobe 7 and a short lobe 8. In order to collect cervical cell samples for determining whether any abnormal cells are present, spatula 5 is held by handle 6 and inserted into the vagina until the spatula's short lobe 8 is positioned within the patient's endocervical canal entrance and the spatula's long lobe 7 is positioned against the exocervix. Long lobe 7 is then rotated about the exocervix with the short lobe essentially pivoting in the endocervix canal entrance As such, the long lobe scrapes and collects cells from the surface of the exocervix. The spatula is then withdrawn from the patient and the cells having been collected on the spatula are then removed therefrom and prepared for examination.

Since the spatula's short lobe 8 merely pivots about the endocervical canal entrance, it scrapes and thus collects very few cells from the endocervix. Accordingly, many physicians use other devices to collect endocervical cell samples. FIG. 1 also illustrates an endocervical brush 10 which is one of the more commonly used devices for endocervical sampling. One such brush is sold by International Cytobrush, Inc. under the trademark "Cytobrush". Brush 10 has a thin cylindrical stem-like handle 11 which is about 7½" long. One end of handle 11 is provided with a generally cylindrical brush portion 12 which is generally about ¾" long and about ¼" in diameter. Drs. Bergeron and Ferenczy point out on page 60 of their article that endocervical samples are taken by inserting the brush into the endocervical canal and then slowing rotating it one-half to one full turn. The brush is then removed from the endocervical canal and a pap smear is prepared by rolling and twisting the brush on a glass slide.

Figure 2:
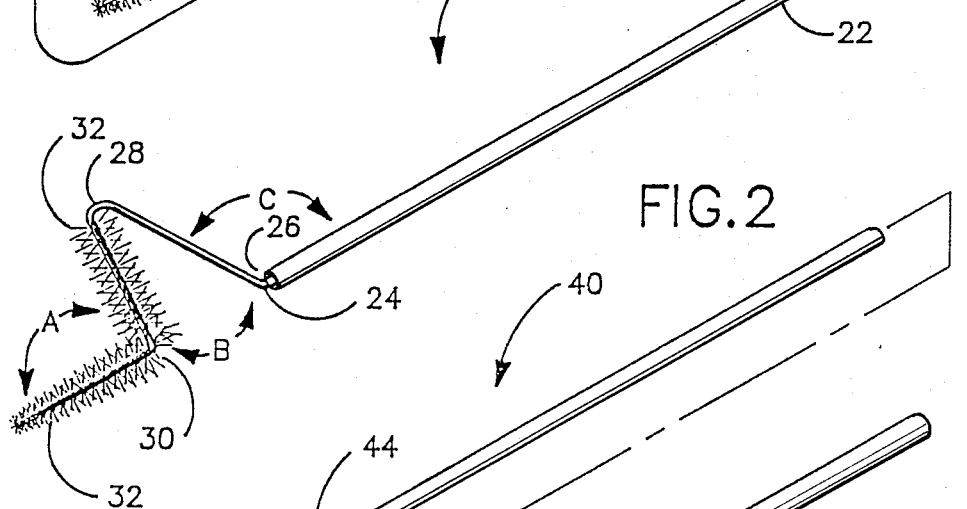
FIG. 2 is a perspective view of a preferred embodiment of the present invention for scraping cytology cell samples from the endocervix and exocervix simultaneously.

FIG. 2 illustrates a preferred embodiment of a brush 20 of the present invention which is used for collecting cytology cell samples from the uterine endocervix and exocervix simultaneously. Brush 20 includes a handle 22 preferably made from a suitable material, such as, plastic, which is mounted on a shaft 24. It can also be seen that shaft 24 is bent in three places which are identified as bends 26, 28 and 30. Brush 20 is provided with a plurality of radially projecting bristles 32 which extend from bend 28 to the distal end of the brush. The bristles extending between bend 30 and 28 define a generally cylindrically shaped cell collecting surface which is referred herein as the intermediate bristled section of brush 20. It can also be seen that bristles 32 gradually taper from bend 30 to the brush's distal end and, as such, define a generally conical cell collecting surface which is referred to herein as the distal bristled section of the brush. The nonbristled area of shaft 24 between bends 28 and 26 is referred to herein as the intermediate offset section of the brush. The diameter of the intermediate bristled section (i.e. its brush portion) is preferably about ¼". The diameter of the distal bristled section preferably tapers from about ¼" at bend 30 to approximately ⅛" at the brush's distal end.

Bristles 32 are secured to shaft 24 in the conventional helically wound manner (not shown). Accordingly, those skilled in the relevant art will recognize that shaft 24 comprises a pair of strands twisted together. The bristles are tightly secured to the shaft by being interposed between the twisted strands of the shaft.

Figure 4:
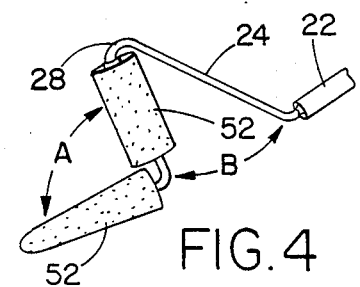
FIG. 4 is a fragmentary perspective view of an alternative device wherein the collecting surfaces are sponge-like closed cell foam or cotton swab material.

While the cell collecting surfaces are bristled in the illustrated embodiment it should be understood that they could be made in accordance with the present invention from material 52 which is suitable for collecting or scraping cells from the respective cervical surfaces. Such materials include closed cell foam materials such as urethane and polyurethane as shown in FIG. 4. Other possible materials include sponge-like materials and cotton-like materials such as a cotton swab.

Returning to FIG. 2, bend 30 defines an included angle A between the distal and intermediate bristled sections which is less than 90°, preferably about 85°. Bend 26 between the nonbristled intermediate offset section and the handle section of brush 20 also preferably defines an included angle C of about 100°. Included angle B defined by bend 28 between the intermediate sections is preferably 10° or greater. In addition, the portions of shaft 24 extending through the distal bristled section and the handle section are preferably axially aligned. Further, the height of the offset portions is preferably ¾" as measured from bend 28 to an imaginary line extending between the angled axis of the handle and distal shaft. A brush manufactured as described will conform to the shape of most womens uterine cervixes. However, shaft 24 may be bent to conform to an irregularly shaped cervix. The angle of the bends may also be altered by the physician to custom fit each patient, as required.

In using brush 20 of the present invention, the patient's vaginal cavity is first opened wide, preferably with a vaginal speculum. This permits brush 20 to be easily inserted into the vaginal cavity. The attending physician can also look into the vaginal cavity to see whether the exocervix of the patient is unusually shaped, and if so the physician can bend the brush so that it conforms to the irregularly shaped exocervix. The physician then inserts the brush into the patient's vaginal cavity until the distal bristled end of the brush is inserted within the endocervical canal and the intermediate bristled section of the brush is in contact with the exocervix. The intermediate bristled section should be in contact with the exocervix along its entire length (i.e. from bend 30 to bend 28). If it is not, it should be bent as previously described until it makes such contact. The physician then rotates the brush by rotating the brush handle with his hand so that the bristles of the intermediate bristled section scrape cell samples from the exocervix. As this occurs, cell samples will also be scraped from the endocervical canal walls by the distal bristled section of the brush which will be rotating within the endocervical canal as the brush rotates. After a suitable sample of cells is collected from the endocervix and exocervix, generally after one or two rotations of the brush, the brush is withdrawn from the vaginal cavity. The cell samples on the bristles of the respective brush portions are then removed from the bristles. Since the endocervical and exocervical samples are preferably analyzed separately, the endocervical cells on the distal bristled portion of the brush are removed by smearing them along the length of a first glass side which preferably is done by slowly rotating the distal end of the brush on the slide. The exocervical cells on the intermediate bristled portion of the brush are removed therefrom similarly by smearing them along the length of a second glass slide. The cells of both slides are then placed in a chemical fixative to preserve the cells until they are examined by a pathologist. The pathologist prepares the cells for examination generally by staining them with a Papanicoloff stain. The cells are then examined by the pathologist under a microscope to determine if any abnormal cancerous, precancerous or virally diseased cells are present.

A brush similar to that described in FIG. 2 was tested and found to collect exceedingly good samples, particularly exocervical samples. In fact, the exocervical samples contained on average approximately five times as many cells as those collected by the conventional wooden spatula. These large samples will enhance the physician's ability to more accurately detect the presence of abnormal cancerous and precancerous cells. The samples have also been large enough to enable physicians to detect the presence of virally diseased cells such as herpes.

Figure 3:
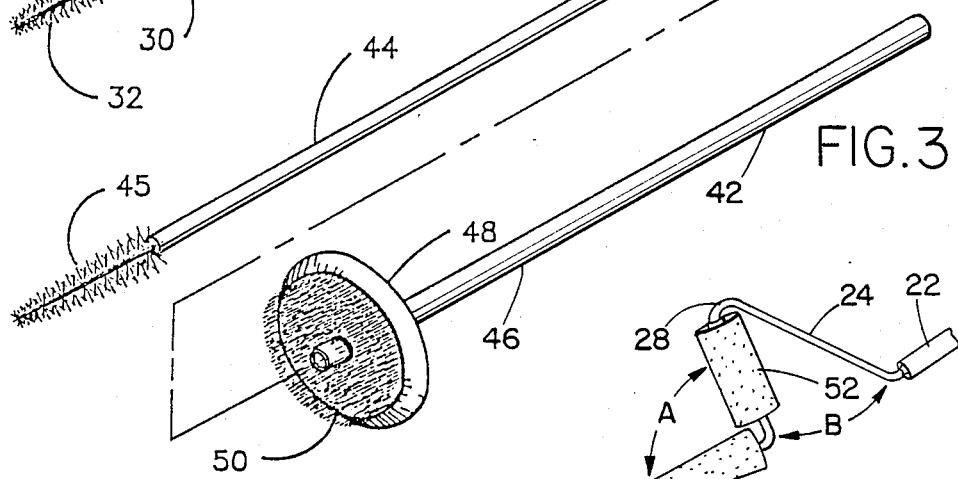
FIG. 3 is an exploded perspective view of another embodiment of the present invention for scraping cytology cell' samples from the endocervix and exocervix simultaneously.

FIG. 3 illustrates an alternative brush 40 of the present invention for collecting cell samples from the exocervix and endocervix simultaneously. Brush 40 is provided with two cell collection surfaces, an exocervical brush portion 42 and an endocervical brush portion 44 having bristles 45 at the distal end. While bristled, it should again be understood that other materials suitable for collecting cells could also be used such as urethane or polyurethane.

Endocervical brush portion 44 is similar to the endocervical brush described in FIG. 1, i.e., brush 10. Exocervical brush portion 42 is provided with a hollow shaft 46 which is sized and configured to telescope over the shaft of the endocervical brush portion 44 and fixedly or frictionally engage therewith (i.e., by interference fit) to enable the shafts to rotate together when rotated by an attending physician. Fixed engagement could also be provided by making shallow shaft 46 out of a flexible material which would enable it to compress and frictionally engage the surface of shaft 44 when grabbed by a physician. Interlocking ribs on shafts 44 and 46 could also be employed to provide fixed engagement between the shafts.

Returning to FIG. 3, it can be seen that exocervical brush portion 42 is provided with a disc 48 which is axially disposed on hollow shaft 46 at one end thereof. Disc 48 is provided with bristles 50 on one side and is preferably about 1½" in diameter. Bristles 50 form a generally planar brushing surface. In addition, bristles 50 are long enough (preferably ⅜" long), to enable the brushing surface to conform to the surface of the exocervix, even an irregularly shaped exocervix.

Use of brush 40 is similar to that of brush 20 previously described. The attending physician (after having opened the patient's vaginal cavity with a vaginal speculum) inserts the brush into the vaginal cavity until the endocervical brush portion is located within the endocervical canal and the brushing surface of disc 48 is positioned against the patient's exocervix. The brush is then rotated one or two times to scrape cell samples from the respective endocervix and exocervix. The brush is then withdrawn from the vaginal cavity and the two brush portions, (i.e., exocervical brush portion 42 and endocervical brush portion 44) are separated. Cell samples on the exocervical brush portion are preferably smeared onto one slide and the cell samples from the exocervical brush portion are preferably smeared on another slide. The slides are then prepared and examined to determine if any abnormalities exist.

The invention has been described in detail with particular reference to two preferred embodiments thereof, but it will be understood that variations and modifications can be effected within the spirit and scope of the invention.

I claim:

1. A cervical cytology device for simultaneously collecting cytology cell samples from the endocervix and exocervix, said device comprising:

a handle for manipulating and rotating said device and having a handle shaft bent to provide a proximally extending handle portion and a laterally extending offset portion;

an intermediate region, with a shaft surrounded by cell collecting means attached at one end to said laterally extending offset portion of said handle and having a surface sized and configured to scrape cytology cell samples from the exocervix when said device is rotated and said intermediate collecting means is in contact with the exocervix;

a distal region with a shaft surrounded by cell collecting means attached to said shaft of said intermediate cell collecting means, said collecting means having a surface sized and configured to scrape cytology cell samples from the endocervix when the device is rotated and said distal collecting means is in contact with the endocervix;

said intermediate region shaft being integral with said distal region shaft but extending laterally from said distal region shaft said handle portion being axially aligned with said shaft of said distal region.

2. A device, as claimed in claim 1, wherein:
the included angle is about 85°.

3. A device, as claimed in claim 1, wherein:
said device is rigid yet bendable to conform to the shape of a particular exocervix and endocervix to be retains its shape until it is bent again.

4. A device as claimed in claim 1, wherein:
at least one of said cell collecting means includes bristles forming a brushing surface for collecting cytology cell samples.

5. A device as claimed in claim 1, wherein:
at least one of said cell collecting means includes closed cell foam for collecting cytology cell samples.

6. A device as claimed in claim 5, wherein:
said closed cell foam is selected from the group consisting of urethane or polyurethane.

7. A device as claimed in claim 1, wherein:
at least one of said cell collecting means includes sponge-like material for collecting cytology cell samples.

8. A device as claimed in claim 1, wherein:
at least one of said cell collecting means includes a cotton swab or cotton-like material for collecting cytology cell samples.

9. A device, as claimed in claim 1 wherein:
said intermediate region shaft extends laterally from said distal region shaft at an included angle which is less than 90°.

* * * * *